United States Patent [19]

Lennon et al.

[11] Patent Number: 5,012,229

[45] Date of Patent: Apr. 30, 1991

[54] USER WEARABLE PERSONAL/MEDICAL INFORMATION DEVICE

[75] Inventors: Charles A. Lennon, 37 Park Ave., New York, N.Y. 10016; George Lowe, Bergenfield, N.J.

[73] Assignee: Charles A. Lennon, New York, N.Y.

[21] Appl. No.: 256,231

[22] Filed: Oct. 11, 1988

Related U.S. Application Data

[63] Continuation of Ser. No. 44,010, Apr. 29, 1987, abandoned.

[51] Int. Cl.$^5$ .............................................. G09F 9/00
[52] U.S. Cl. ...................................... 340/706; 40/447; 368/10; 364/413.01; 221/2; 340/799
[58] Field of Search ............... 340/712, 711, 706, 799; 368/10; 40/21 C, 446, 447, 586, 448; 128/69 D, 706; 364/413, 414, 415, 569, 413.01, 413.03; 221/2

[56] References Cited

U.S. PATENT DOCUMENTS

| | | | |
|---|---|---|---|
| 3,285,291 | 5/1973 | Piguet | 340/712 |
| 3,805,427 | 4/1974 | Epstein | 40/21 |
| 3,848,112 | 11/1974 | Weichselbaum et al. | 235/61.7 |
| 3,864,856 | 2/1975 | McManus | 40/21 |
| 3,937,004 | 2/1976 | Natori et al. | 58/152 |
| 3,938,139 | 2/1976 | Day | 340/324 |
| 3,965,589 | 6/1976 | McDermott | 40/21 |
| 4,121,574 | 10/1978 | Lester | 364/415 X |
| 4,159,417 | 6/1979 | Rubincam | 340/706 |
| 4,205,312 | 5/1980 | Nelson | 340/792 |
| 4,301,512 | 11/1981 | Keith et al. | 364/801 |
| 4,303,996 | 12/1981 | Schmitz | 368/82 |
| 4,354,260 | 10/1982 | Planzo | 368/10 |
| 4,365,243 | 12/1982 | Pesotto et al. | 340/712 |
| 4,369,440 | 1/1983 | Piguet et al. | 340/712 X |
| 4,371,945 | 2/1983 | Karr et al. | 364/561 |
| 4,406,290 | 9/1983 | Walbeoffe-Wilson et al. | 128/690 X |
| 4,477,797 | 10/1984 | Nakagir | 340/712 X |
| 4,489,731 | 12/1984 | Baumberg | 128/690 |
| 4,504,153 | 3/1985 | Schollmeyer et al. | 364/569 |

Primary Examiner—Alvin E. Oberley
Attorney, Agent, or Firm—Leo Zucker

[57] ABSTRACT

A wearable personal/medical information device includes a data display with an associated legend display. A memory stores items of personal and/or medical information relating to the person wearing the device. Upon operation of a switch, the stored information is displayed with the personal/medical information indicated by the data display, and a corresponding legend indicated by the legend display. In a preferred embodiment, certain data such as medical information is preset in a read only memory, and other data which the user may change from time-to-time is stored in a read/write memory.

7 Claims, 4 Drawing Sheets

FIG.1
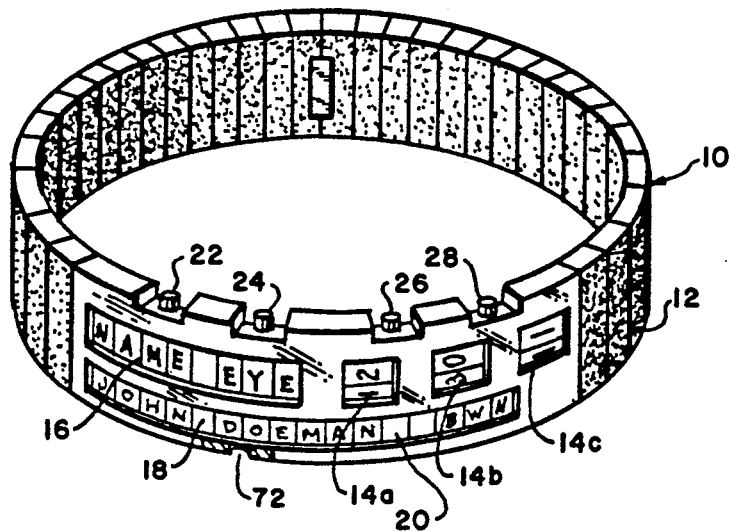
FIG.4
| ADDRESS LINE | | | | | | | | |
|---|---|---|---|---|---|---|---|---|
| 1 | N | A | M | E | | E | Y | E |
| 2 | S | S | N | | B | D | A | Y |
| 3 | M | D | N | A | M | T | E | L |
| 4 | D | I | S | E | A | S | E | S |
| 5 | A | L | L | E | R | G | Y | |
| 6 | H | T | | W | T | | B | L D |
| 7 | R | X | 1 | | D | O | S | E |
| 8 | R | X | 2 | | D | O | S | E |
| 9 | E | K | G | | C | H | A | R |
| 10 | E | M | E | R | | T | E | L |
| 11 | A | X | C | A | R | D | N | O |
| 12 | M | C | C | A | R | D | N | O |
| 13 | P | H | O | N | E | | 1 | |
| 14 | P | H | O | N | E | | 2 | |
| 15 | J | A | N | E | S | I | Z | E |
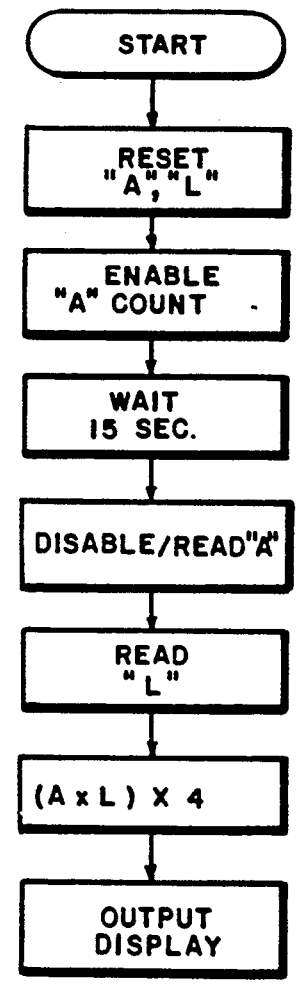
FIG.5

USER WEARABLE PERSONAL/MEDICAL INFORMATION DEVICE

This application is a continuation, of application Ser. No. 044,010, filed Apr. 29, 1987, now abandoned.

BACKGROUND OF THE INVENTION

1. Field Of The Invention

The present invention relates generally to identification devices worn or carried on one's person, and more particularly to such a device which displays personal and/or medical information pertaining to the person wearing or carrying the device in response to movement of a switch. The term "wearer" will hereafter imply an individual who either wears or carries the present device on his or her person.

2. Description Of The Known Art

A user programmable message watch is known from U.S. Pat. No. 4,303,996, issued Dec. 1, 1981. The watch includes a light emitting diode (LED) display and is capable of displaying a pre-programmed message of up to 5 words one word at a time upon depression of a push button, according to the patent. It is also known from U.S. Pat. Nos. 3,805,427 (Apr. 23, 1974) and 3,864,856 (Feb. 11, 1975) to provide medical emergency data on a card held in a compartment of a watch strap or bracelet.

It will be appreciated that the mentioned devices are not suitable for storing and displaying extensive personal and/or medical information data.

Also known is a so-called Med-Alert bracelet which has information engraved into the bracelet. Such information can be a combination of personal and medical data. The Med-Alert bracelet, as well as the watch straps or bracelets which hold emergency data cards, have the disadvantage that any change in the data necessitates a whole new bracelet or card.

SUMMARY OF THE INVENTION

An object of the invention is to Provide a wearable information device capable of immediately displaying personal identification and pertinent medical information upon a simple button operation.

Another object of the invention is to allow an individual to have personal and medical information on his or her person for immediate retrieval by anyone requiring it, e.g., paramedics, medical personnel, or police.

A further object of the invention is to provide a personal/medical information device capable of storing a far greater quantity of data than the known devices, at least some of which data can be easily changed or updated by the user.

According to the invention, a personal/medical information device caPable of being worn or carried on the person, includes means for storing in the form of data characters items of information relating to a user of the device, data display means for providing a display of the items of information, and legend display means for displaying identifying legends in association with the information displayed by the data display means. Operate switch means initiates the display of the items of information together with the legends by both of the display means, and processor means coupled to the storing means and both display means reads out in response to operation of the switch means, the data characters from the storing means and causes corresponding items of information to be displayed with associated legends on both of the display means.

The various features of novelty which characterize the invention are pointed out with particularity in the claims annexed to and forming a part of the present disclosure. For a better understanding of the invention, its operating advantages and specific objects attained by its use, reference should be had to the accompanying drawing and descriptive matter in which there are illustrated and described preferred embodiments of the invention.

BRIEF DESCRIPTION OF THE DRAWING

In the Drawing:

FIG. 1 is a perspective view of a personal/medical information device according to the invention;

FIG. 4 shows exemplary legends displayed by legend display means when associated information items are displayed by data display means in the device of FIG. 1;

FIG. 5 is a flow chart showing operations carried out by the micro control unit of FIG. 3 when in a heart rate monitor mode;

DETAILED DESCRIPTION OF THE INVENTION

FIG. 1 is a perspective view showing an overall appearance of a personal/medical information device 10 according to the invention.

Figure 2:
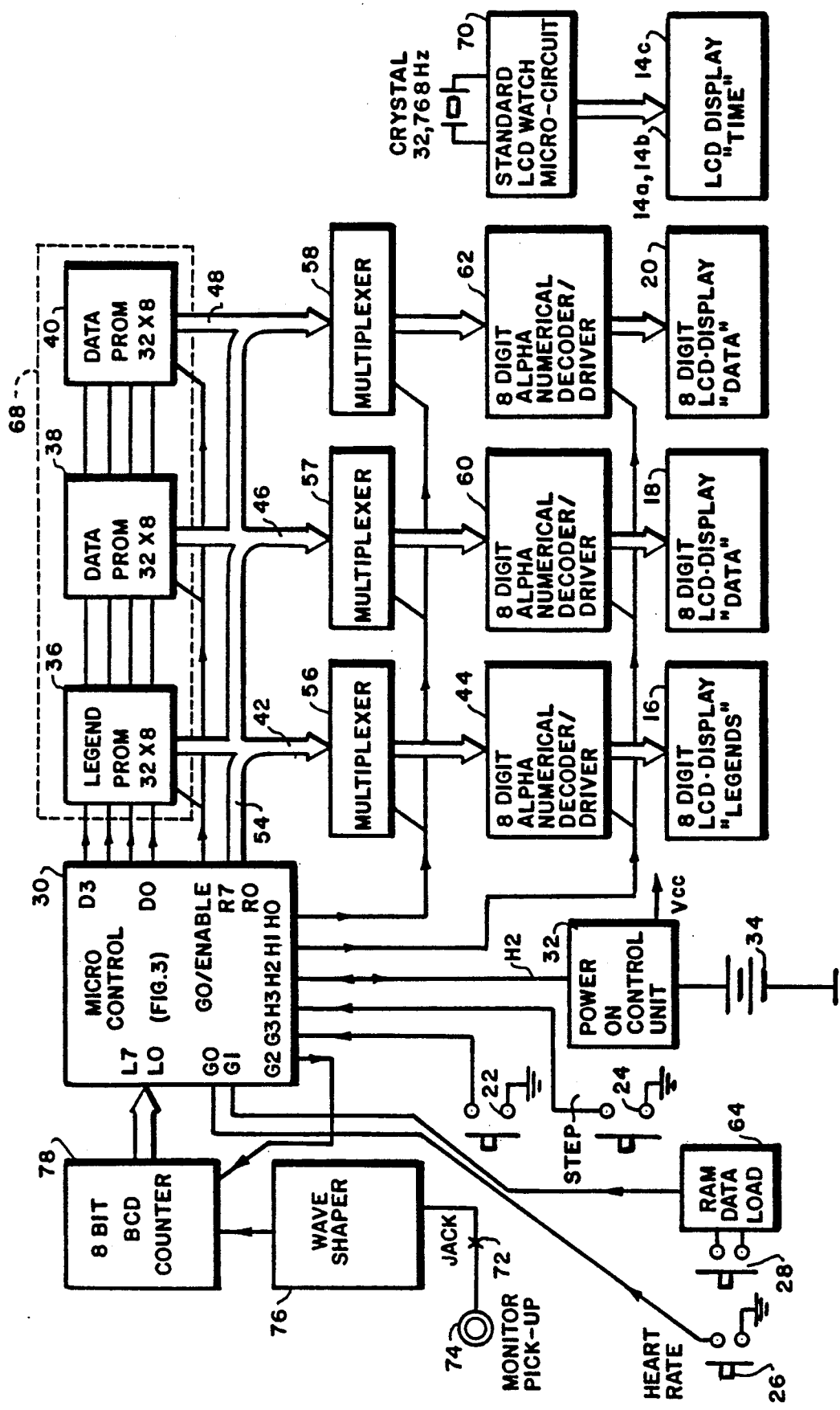
FIG. 2 is a schematic block diagram showing an arrangement of electronic components in the device of FIG. 1.

In the illustrated embodiment, the device 10 is in the form of an expandable link wrist band 12, and features time and/or date numeric displays 14a, 14b and 14c which are preset by means not shown in the figure. The time/date displays 14a, 14b, 14c and associated circuitry shown in FIG. 2 are provided for the convenience of the wearer of the device 10. The time/date displays may, alternatively, be in the form of a single conventional 3½ digit LC display so as to require less area on the surface of the wrist band 12, as in the embodiment of FIG. 6. Further, the time/date displays in either embodiment may be provided with suitable means (not shown) to operate in a stop watch mode.

A legend display 16 is arranged on the wrist band 12 for presenting identifying legends in association with personal/medical information displayed by a pair of in-line 8-digit displays 18, 20. That is, the information displays 18, 20 allow for up to 16 digits of information data to be displayed in association with each identifying legend. Examples of legends presented by the display 16 are set out in FIG. 4, in a typical order presented when the device 10 is operated by the user.

Character data for each legend is stored at specific addresses in memory areas of the device 10, as explained in detail below. In the example shown in FIG. 4, the legend at the first address "NAME EYE" identifies data when indicated on the information displays 18, 20 as being the wearer's name and eye color. The second address legend "SSN BDAY" identifies the user's Social Security number and birthday. The remaining legends signify:

(3) user's doctor and doctor's phone number;

(4) any diseases (e.g., diabetes) suffered by the user;
(5) any allergies of the user;
(6) the user's height, weight and blood type;
(7) a first prescription drug and dosage;
(8) a second prescription drug and dosage;
(9) any EKG characteristic peculiar to the user;
(10) a phone number of someone to call in case of emergency;
(11) a first bank card number belonging to the user;
(12) a second bank card number;
(13) a first phone number important to the user;
(14) a second phone number; and
(15) a clothing size(s) for the user to recall when buying a gift.

A first push button 22 (FIG. 1) at the side of the wrist band 12 initiates an operational cycle during which the legends are presented in a determined time sequence in association with personal/medical information, by the displays 16, 18 and 20. A second push button 24 adjacent the first button 22, enables the user to select and hold items of information, one at a time, when presented by the displays 16, 18, 20. A third push button 26 initiates a heart rate monitor and display mode, as will be explained in connection with FIG. 5. A fourth push button 28 enables the wearer of the device 10 to load certain items of personal information and to update or change the information at a later date.

FIG. 2 is a block diagram of electronic components contained within the device 10, and their interconnections. A processor or micro control unit 30 is programmed to control operation of various components in FIG. 2 in a desired manner upon depression of the first push button 22. Micro control unit 30 may be one which is commercially available, for example, device type COP-440 manufactured by National Semiconductor, Santa Clara, Calif.

Depression of the first push button 22 sends a ground level signal to the micro control unit or processor 30, to start an internal operational control cycle. First, by way of an "H" register shown in FIG. 3, an I/0 port signal H2 is sent to a power on control unit 32 (FIG. 2). The power on control unit 32 then supplies $V_{CC}$ voltage to other components in FIG. 2 as obtained from a power source, e.g., a battery 34 connected to the power on control unit 32.

Micro control unit 30 then generates by way of an internal "D" register (FIG. 3) a first address to each of three programmable read only memories 36, 38 and 40. Memory 36 serves as a legend memory and outputs data over a legend data bus 42 for processing by an 8-digit alpha numeric decoder/driver 44. Driver 44 generates corresponding display signals which are coupled to the legend display 16. Memories 38 and 40 permanently store in the form of data characters items of information relating to the wearer of the device 10, and generate the data in response to address signals from the micro control unit 30 over information data buses 46, 48.

Figure 3:
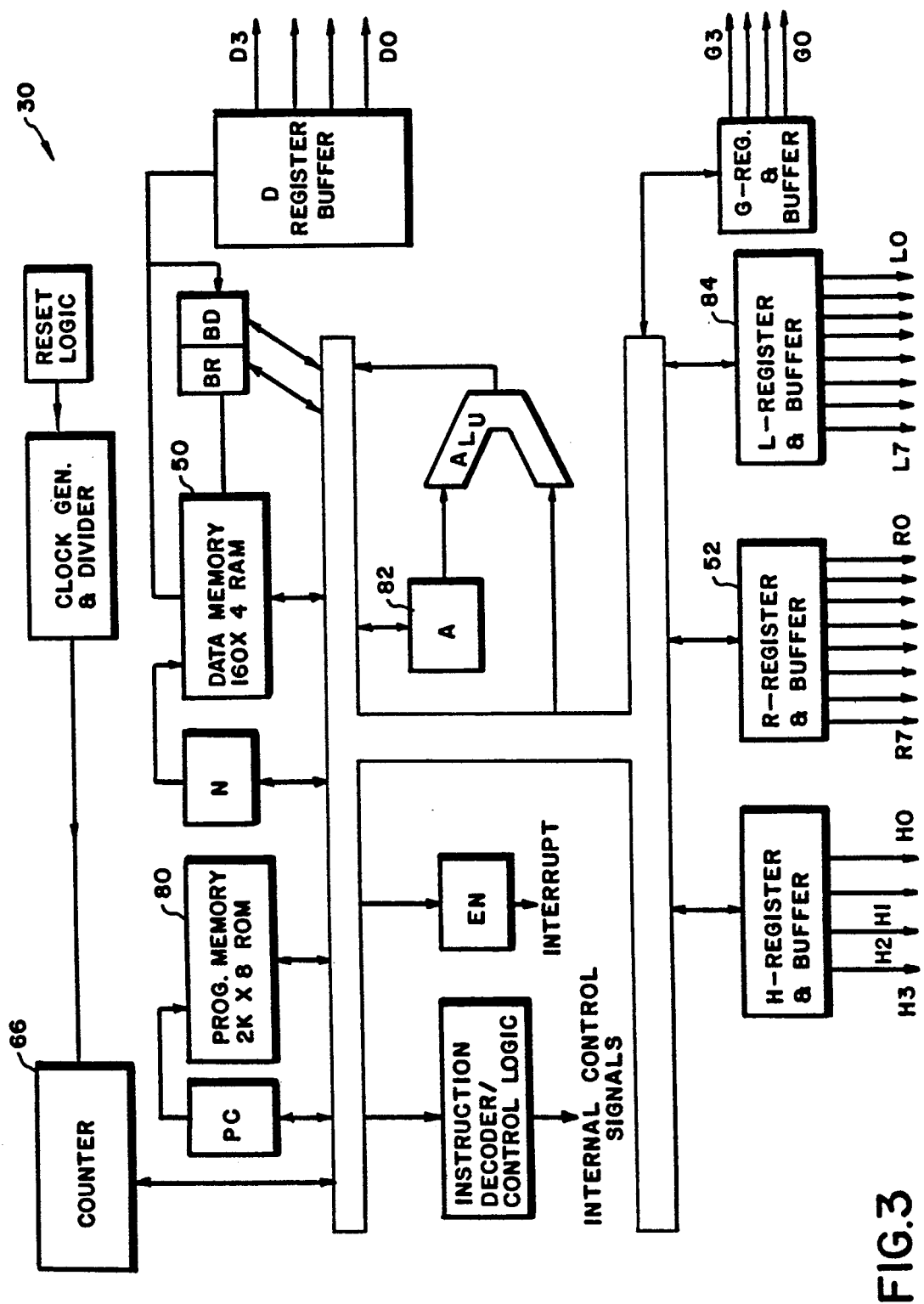
FIG. 3 is a block diagram of logic components within a micro control unit in FIG. 2.

Certain items of information which a wearer of the device 10 may want to change or update are loaded into an internal data read/write memory or RAM 50 in the micro control unit 30 (see FIG. 3). Data stored in the internal RAM 50 is output from an "R" register 52 (FIG. 3) over a data bus 54 (FIG. 2). Multiplexers 56, 57, 58 are coupled to the data bus 54 and to the legend and information data buses 42, 46, 48 as represented in FIG. 2. Each of the multiplexers 56, 57, 58 is coupled through an associated 8-digit alpha numeric decoder/driver 44, 60, 62 to a respective 8-digit data display 16, 18, 20.

Loading of information data with associated legends into the internal data RAM 50, is carried out by operation of the fourth push button 28 which is coupled to a RAM data load section 64. By using manual step switching, the user causes consecutive numbers to be displayed one at a time on a selected one of the displays 16, 18, and 20. The displayed numbers correspond to a desired address location of the internal data RAM 50 between, for example, addresses 11 through 15. Once a desired address is displayed, the user then pushes in and holds the second push button 24 until desired numbers (counted sequentially by a counter 66 in the micro control unit 30) corresponding to data characters to be stored at each digit of the selected address are indicated on the display. That is, numbers 0–9 when indicated may correspond to the same numeric data, and numbers 10–35 may correspond to letter data of A to Z, respectively, when indicated on the display. When the appropriate number is displayed, button 24 is released and depressed again to allow a data character to be selected and loaded for the next digit.

Rather than loading data into the RAM 50 by way of the second push button 24, a jack (not shown in FIG. 1) may be provided on the wrist band 12 and connected to the micro control unit 30 for inputting desired data at selected addresses of the RAM 50 when the RAM data load routine is initiated by button 28, and a hand-held keyboard device is plugged in. Such an arrangement, shown in the embodiment of FIGS. 6 and 7 allows new or updated information to be entered more quickly with the aid of a portable alpha-numeric keyboard device, and will be described further below.

Provision thus is made in the present device 10 for storing critical medical or personal information which is not to be altered or tampered with, in the read only memories 36, 38 and 40. The memories 36, 38, 40 may be in the form of a removable chip 68 and programmed by a suitable outside facility once a purchaser of the device 10 completes a data information card and sends the card to the facility. The programmed chip 68 is then returned to the purchaser and installed in the device 10 much like a new watch battery. The outside facility may also issue a personal code number to the purchaser, so that he or she may order another memory chip 68 with new or updated information burnt in, by calling an "800" number and identifying him/herself with the issued code number. The old chip 68 would be discarded and replaced by the new one.

A standard watch micro-circuit 70 is provided for driving the time/date numeric displays 14a, 14b, 14c. As mentioned, micro-circuit 70 may include means for allowing the time/date displays to function as a stop watch.

A jack 72 is provided on the device 10 for connection with an external heart monitor pick-up 74 (FIG. 2). Within the device 10, a wave shaper circuit 76 has an input connected to the jack 72 and provides a suitably formed pulse to an input of an 8-bit BCD counter 78 in response to each monitored heart beat. The BCD counter is connected to a "L" register of the micro control unit 30 (see FIG. 3), and a heart rate Program Preset in a read only memory 80 in the control unit 30 enables the device 10 to display the monitored heart rate in, for example, counts per minute. FIG. 5 is a flow chart showing operations carried out within and by the micro control unit 30 when a heart rate monitor mode is selected upon depression of the third push button 26.

When the push button 26 is depressed and the monitor pick-up 74 is plugged into the jack 72, a ground signal is applied to the control unit 30 via a "G" register. The internal ROM 80 of the control unit 30 will execute the heart rate program as shown in FIG. 5. In the illustrated embodiment, a pulse count is maintained only for 15 seconds and the accumulated total is multiplied by 4. In FIG. 5, "A" is an internal clock/timer 82 in the control unit 30 (FIG. 3), and "L" corresponds to the monitored/counted pulses provided to an L register 84 by the BCD counter 78 in FIG. 2.

Operation of the present device 10 is as follows.

After depression of the first button switch 22 and the supply of power to electronic components within the device 10, the micro control unit 30 outputs via its D register an initial address to each of the three ROMs 36, 38, 40 as mentioned above. Stored information corresponding to the initial address is then generated by the memories 36, 38, 40 and coupled to the corresponding alpha numeric decoder/drivers 44, 60, 62. A total of 24 digits or characters of information is provided to the displays 16, 18, 20.

After a determined time, for example, 3 seconds, the control unit 30 steps to a next address line for the ROMs 36, 38, 40. After a second wait time, the operation is repeated until a determined address line, e.g., 11, is reached. In the illustrated embodiment, address lines 11 through 15 correspond to certain personal information which is subject to change or updating and, thus, is stored within the internal RAM 50 of the control unit 30. Thus, under the operating program for the control unit 30, the multiplexers 56, 57, 58 switch from passing data from the ROMs 36, 38, 40 to the displays 16, 18, 20, to passing the data stored in RAM 50 as output from the control unit 30 through its R register 52. After the last address line is reached and the corresponding display completed, the automatic operation ends.

In a manual mode of operation, when the second push button switch 24 is depressed, information stored in the ROMs 36, 38, 40 and the RAM 50 is displayed one line at a time and will change only when the button 24 is again depressed. If a display is left on more than 10 seconds at any one address, the control unit 30 is programmed to shut down so as to conserve battery power.

In the heart-rate monitor mode, the third push button 26 is depressed, and the program represented in FIG. 5 and contained in the ROM 80 (FIG. 3) will be initiated. A selected one of the displays will show the number of heart beats per minute. About 15 seconds into the display, the system will automatically shut down.

Although the present device 10 is shown embodied in the form of a wrist watch, it will be appreciated that it may also take on the form of a bracelet or a neck chain medallion. Most all persons who would want certain personal/medical information available on his or her person for immediate retrieval will have use for the present device. The surge in interest in personal health and fitness within the United States alone reflects a current need for the present device. Parents can use the device in the form of an identification bracelet for their children, and the military may find the present device of value for its personnel, particularly for storing and displaying certain important data when needed–i.e., a potential modern day "dog tag".

Pet owners may use the device as an electronic identification and information tag.

Moreover, the permanently stored information may be standardized to facilitate proper medical attention. For example, if the wearer is unconscious and a paramedic must know the victim's blood type immediately, it may be common knowledge that such information is at address line 6. After turning the device 10 on and operating button 24 rapidly to display address line 6, the victim's blood type is identified along with his/her height and weight.

Figure 6:
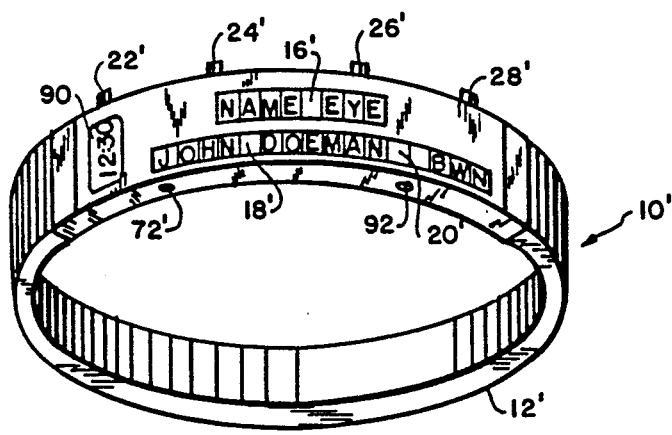
FIG. 6 is a perspective view of modified version of the personal/medical information device in FIG. 1.
Figure 7:
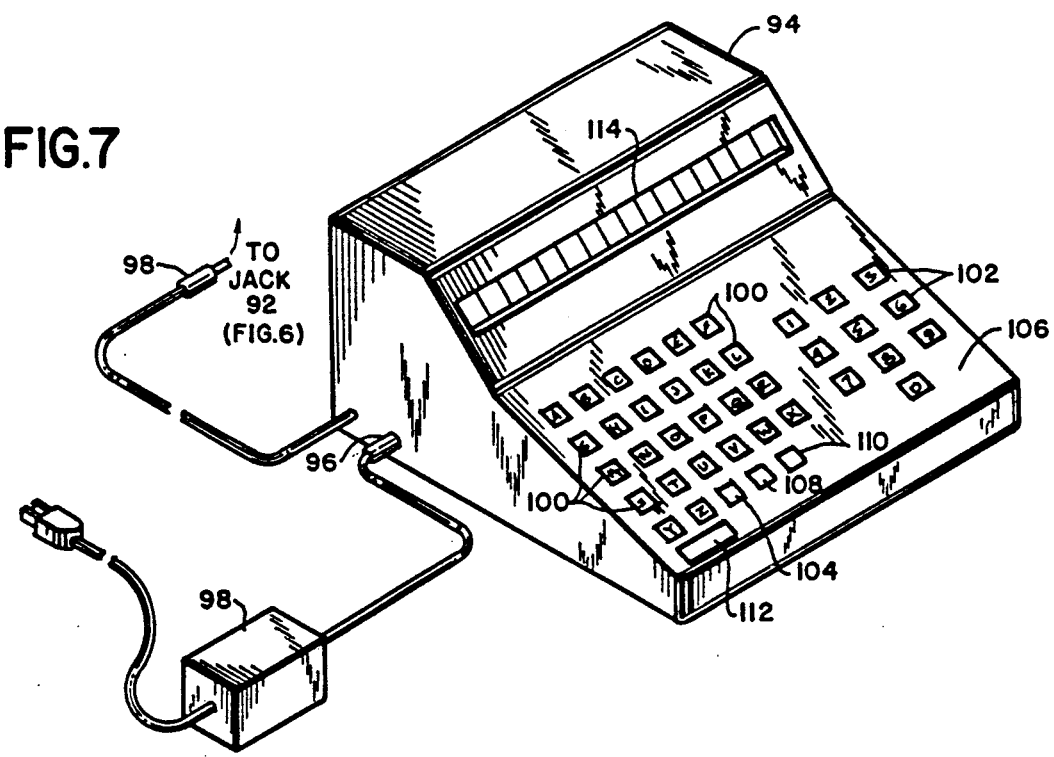
FIG. 7 is a perspective view of a portable data character generating device for loading data characters in a memory portion of the present information device.

FIGS. 6 and 7 show an embodiment in which provisions are made for storing or updating personal items of information in the RAM 50 of the present device, through use of a separate alpha/numeric keyboard device.

FIG. 6 is a perspective view of a modified version 10' of the personal/medical information device 10 in FIG. 1, and parts similar to those of the device 10 have corresponding reference numerals. Device 10' features a single 3½ digit LC display 90, and a personal data input jack 92 coupled to the internal micro control unit of the device.

FIG. 7 shows a portable alpha/numeric keyboard device 94 for generating data characters to be stored at selected addresses of the RAM in the control unit of the device 10'. The keyboard device 94 is preferably battery operated, and provided with a suitable AC charger 96 which connects to the device 94 with a conventional plug 96 for recharging and/or use when an AC outlet is available to the user.

The keyboard device 94 connects with a plug 98, to the jack 92 on the body of the device 10', and data character generation and storage take place after the user depresses corresponding alphabet keys 100 and numeral keys 102. An ON/OFF button 104 is provided on an operating panel 106, together with other operation buttons 108, 110 which enable the user to select an address of the RAM to be written, and load corresponding legend and information data at the selected address. A space key 112 generates a blank if desired at any given display digit.

A 16-digit LC display 114 allows the user to preview and edit the data characters while stored in an internal buffer, and before writing in the RAM of the device 10'. Further structural and operational details of the keyboard device 94 would be apparent to one skilled in the art with the benefit of the present disclosure.

While the foregoing description represents preferred embodiments of the invention, it will be obvious to those skilled in the art that various changes and modifications may be made, without departing from the true spirit and scope of the invention.

What is claimed is:

1. A personal/medical information device capable of being carried on a person, comprising:
   display means including
      information display means for providing a display of items of vital personal or medical information pertaining to the person, and
      legend display means for displaying items of identifying legends in association with the items of vital information displayed by said information display means;
   operate switch means for initiating displays of said items of vital information and said items of identifying legends by said display means;
   storing means including
      detachably mountable read only memory means for storing at certain first address locations preset items of vital personal or medical information data and preset items of associated legend data, wherein items of items of vital information data and associated legend data can be read out for display from the first address locations of the read only memory means, and read/write memory means for storing at certain address locations different from said first address locations, items of other information data and associated items of identifying legend data that can be set and updated by the person, and including data input means coupled to the read/write memory means for enabling the person to set and update only the other information and associated legend data, wherein said items of other information and associated legend data can be read out for display from the second address locations of the read/write memory means; and processor means responsive to said operate switch means for reading out said items of vital information data, other information data and associated identifying legend data, selectively from one of said first address locations of the read only memory means and said second address locations of the read/write memory means, and for enabling the display of the selected information data and legend data by said display means.

2. The information device according to claim 1, wherein said data input means includes a counter for producing time-sequenced numeric data for display by said display means, and input switch means for causing character data to be set at said certain addresses in said read/write memory means, wherein the character data corresponds to the numeric data displayed at a time when said input switch means is operated by the user.

3. The information device according to claim 1, wherein said read only memory means comprises a programmable read only memory.

4. The information device according to claim 1, wherein said processor means includes means for displaying each of said items of information data and identifying legend data in a determined time sequence on said information display means in response to a single actuation of said operate switch means by a user.

5. The information device according to claim 1, wherein said operate switch means includes manual step display button means for displaying legend data and information data stored in both of said read only memory means and said read/write memory means, on said legend and said information display means, respectively, in a determined order upon successive operations of said step display button means.

6. The information device according to claim 1, including heart rate monitor means for calculating a monitored heart beat rate, and for displaying the calculation result on said display means.

7. The device of claim 1, wherein said read only memory means is adapted so that the stored items of information data and legend data are incapable of alteration by operation of the device.

* * * * *